(12) United States Patent
Rajasekharan et al.

(10) Patent No.: US 8,383,128 B2
(45) Date of Patent: Feb. 26, 2013

(54) METHOD OF PROTECTING PLANT(S) AND A PROCESS THEREOF

(75) Inventors: Ram Rajasekharan, Bangalore (IN); Vivek Babu Shivegowda, Bangalore (IN); Dodaghatta Krishnarao Venkata Rao, Bangalore (IN)

(73) Assignee: Indian Institute of Science, Bangalore (IN)

( * ) Notice: Subject to any disclaimer, the term of this patent is extended or adjusted under 35 U.S.C. 154(b) by 135 days.

(21) Appl. No.: 12/920,996

(22) PCT Filed: Mar. 3, 2009

(86) PCT No.: PCT/IN2009/000155
§ 371 (c)(1),
(2), (4) Date: Sep. 3, 2010

(87) PCT Pub. No.: WO2009/116083
PCT Pub. Date: Sep. 24, 2009

(65) Prior Publication Data
US 2011/0021615 A1 Jan. 27, 2011

(30) Foreign Application Priority Data
Mar. 7, 2008 (IN) .............................. 587/CHE/2008

(51) Int. Cl.
*A01N 65/00* (2009.01)
(52) U.S. Cl. .................. 424/195.15; 424/405; 514/453; 514/175

(58) Field of Classification Search .................. None
See application file for complete search history.

(56) References Cited

U.S. PATENT DOCUMENTS
6,277,786 B1 8/2001 Rajasekharan et al.

OTHER PUBLICATIONS

Liu (Organic Letters (2006), vol. 8, No. 3, pp. 423-425).*
Geris (Nat. Prod. Rep. (2009), vol. 26, pp. 1063-1094).*
Geris (Chemistry & Biodiversity, (2008) vol. 5, pp. 341-345).*
Abdalla (Transactions of the British Mycological Society (1981), vol. 76, No. 3, pp. 367-370).*
Goswami (Pesticide Research Journal (2007), vol. 19, No. 1, pp. 51-55).*
Kim et al., "Terreulactones A. B, C and D: Novel Acevlcholinesterase Inhibitors Produced by *Aspergilus terreus*," *The Journal of Antibiotics*, vol. 56, No. 4, Apr. 2003, pp. 351-357.
Seifert, "Isolation of Filamentous Fungi," *Isolation of Biotechnological Organisms from Nature*, Chapter 2, Biotechnology and Chemistry Department, Canada, 1990, pp. 21-51.
Raper et al., "*Aspergillus terreus* Group" *The GENUS Aspergillus*, Chapter XXVI, 1965, pp. 567-577.
International Search Report dated Sep. 22, 2009 in International Patent Application No. PCT/IN2009/000155.
International Preliminary Report on Patentability dated Sep. 7, 2010 in International Patent Application No. PCT/IN2009/000155.

* cited by examiner

*Primary Examiner* — Susan Hoffman
(74) *Attorney, Agent, or Firm* — Oliff & Berridge, PLC (57) ABSTRACT

The present invention relates to a method of treating plant(s) against larval pests by the use of terreulactone. It also relates to a process for producing meroterpenoid from fungus *Aspergillus terreus* strain MTCC5390.

7 Claims, 5 Drawing Sheets

METHOD OF PROTECTING PLANT(S) AND A PROCESS THEREOF

FIELD OF THE INVENTION

The present invention relates to the use of meroterpenoids as insecticides. More particularly, the present invention establishes the use of terreulactone A as an insecticide. It also relates to a process for producing meroterpenoid from fungus *Aspergillus terreus* strain MTCC5390.

BACKGROUND AND PRIOR ART OF THE INVENTION

Computational tools are becoming increasingly important to integrate the wealth of structural data with more traditional lead optimization techniques. Amongst them, virtual screening is bringing a more cost-effective approach to drug discovery by using high-performance computing to analyze chemical databases and prioritize compounds for synthesis and assay. Despite the definite potential of some natural products, there is still a problem associated with the targeting selection due to the multitude and chemical diversity of natural products. To overcome this challenge modern computer-aided screening techniques such as biological target modeling coupled together with virtual screening has been extensively used. Further, virtual screening provides enough reliable structural information about the target, or compounds that bind to various biomolecules.

Receptor-based virtual screening (REVS) starts with a 3-D structure of a target protein and a ligand followed by docking to identify potential lead candidates, Docking and scoring algorithms generate subsets of a compound collection with a higher affinity against a target by predicting their binding mode (by docking) and affinity (by free energy). The docking algorithms deal with the prediction of ligand conformation and orientation within the targeted active site of the receptor. Some of the most widely used docking programs in high through put searches are DOCK, FlexX, GOLD, Glide, ICM, FRED and AutoDock.

The aim of this study is to demonstrate the strategy of utilizing computer-aided (in silica) receptor based virtual screening for improved acetylcholinesterase (AchE) inhibitors such as meroterpenoids.

The effective control and protection of desirable plant life is possible through the use of chemicals formulated to provide protection as selective insecticides and pesticides. However, all requirements for effectiveness and selectivity among pesticides have not been satisfied. There are still many demands to satisfy among agriculturalists and others, either for more effective pesticides with selectivity comparable to old pesticides, or for pesticides with a different selectivity.

Enzyme inhibitors are important class of molecules that used as drugs and pesticides. The enzymes acetylcholinesterase (AchE) is involved in the synaptic transmission of the nerve impulse and its inhibition leads to accumulation of the neurotransmitter, acetyl choline leading to over excitation of the postsynaptic neuron. This property of the inhibitor has been exploited to develop newer insecticides against a wide range of insect pests as well as drugs effective against worms and recently a new class of neuroactive drugs against dementia or Alzheimer's disease.

The meroterpenoids are a novel family of fermentation-derived natural products. The meroterpenoids from *Aspergillus terreus* are naturally-occurring as terreulactones A, B, C and D and are synthesized as fermentation products. Terreulactones A, B, C and D are meroterpenoids type compounds that have mixed polyketide-terpenoid structures, which are not common in microbial metabolites. Amongst these terpenoids, terreulactone A is a sesquiterpene meroterpenoid having fused lactone skeleton in its sesquiterpene moiety (Cho et al., 2003). A literature report on terreulactone indicates its potential activity as inhibitor for acetylcholinesterase enzyme in the treatment of Alzheimer's disease. In this respect, acetyl cholinesterase inhibitors have attracted particular attention for other uses as well.

Terreulactone A can be produced from *Aspergillus terreus* through Solid state fermentation using wheat bran as substrate (Mi-Cho et al., 2003—J Antibiotics; 2003:56(4):344-350).

Although number of documents refer to the production of meroterpenoids by culturing different microorganisms, most of them describe fermentation processes where the nutrients are added or mixed in with the microorganism in the culture medium at the beginning of the production process. Generally, (the fixed amount of) these nutrients are therefore gradually used up during fermentation. However, at the beginning of the process, because the nutrients are at relatively high concentrations, production of desired compound is low because the microorganisms use carbon and nitrogen sources to grow, rather than to produce the drug. In such a process, the rate of production of the desired product is largely uncontrollable. Overall production levels are low because in the batch processes, nutrients are in effect supplied only once to the microorganism and so no variation (at least during production) can be made to balance growth of the biomass with production of the fermentation product.

The present disclosure overcomes the limitations associated in the prior art mentioned above.

OBJECTS OF THE INVENTION

The main object of the invention is to develop a method of protecting plant(s) against larval pests by treating the plant(s) with terreulactones.

Another object of the present invention is to obtain a process for production of meroterpenoid(s) through submerged fermentation.

STATEMENT OF THE INVENTION

Accordingly, the present invention is in relation to a method of protecting plant(s) against larval pests, said method comprising step of treating the plant(s) with terrulactones; and a process to obtain meroterpenoid(s) through submerged fermentation, said process comprising steps of: (a) inoculating culture of *Aspergillus terreus* into a sterilized fermentation medium; (b) incubating the inoculated fermentation medium without agitation at stationary conditions to obtain biomass; and (c) extracting the biomass with organic solvent or subjecting the biomass to HPLC to obtain the meroterpenoid(s).

DETAILED DESCRIPTION OF THE INVENTION

The present invention relates to a method of protecting plant(s) against larval pests, said method comprising step of treating the plant(s) with terrulactones.

In another embodiment of the present invention, the terreulactones are selected from a group comprising terreulactone A, terreulactone B, terreulactone C and terreulactone D, preferably terreulactone A.

In yet another embodiment of the present invention, the larval pests are selected from a group comprising lepidoptera, diptera, coleoptera, thysanoptera and hymenoptera, preferably lepidoptera.

In still another embodiment of the present invention, the lepidopteran larvae is *Helicoverpa armigera*

In still another embodiment of the present invention, the terreulactones provide for about 80% to about 85% mortality rate at a concentration of about 8 µg to about 12 µg, preferably about 10 µg.

The present invention relates to a process to obtain meroterpenoid(s) through submerged fermentation, said process comprising steps of:
 a) inoculating culture of *Aspergillus terreus* into a sterilized fermentation medium;
 b) incubating the inoculated fermentation medium without agitation at stationary conditions to obtain biomass; and
 c) extracting the biomass with organic solvent or subjecting the biomass to HPLC to obtain the meroterpenoid(s).

In still another embodiment of the present invention, the meroterpenoid(s) is selected from a group comprising terreulactone A, terreulactone B, terreulactone C and terreulactone D, preferably terreulactone A.

In still another embodiment of the present invention, the biomass is dried before extraction and the dried biomass is extracted with an organic solvent in ratio ranging between 1:2 to 1:20, preferably about 1:10.

In still another embodiment of the present invention, the organic solvent is selected from a group comprising ethyl acetate, methanol, dichloromethane, chloroform, hexane, acetonitrile, preferably ethylacetate.

In still another embodiment of the present invention, the HPLC is carried out using $C_{18}$ reverse phase column at a flow rate of about 0.2 to 1 mL/min, preferably 0.5 mL/min for about 15 to about 60 min, preferably 30 min with acetonitrile and water in the ratio ranging between 30:70 to 70:30 (v/v), preferably 50:50 (v/v) at about 25 deg C. to 35 deg C., preferably 30 deg C.

In another embodiment of the present invention, In silico based molecular docking was performed on acetylcholinesterase for evaluating binding affinities which provides better way of understanding molecular interaction and binding free energy. The molecular docking of terreulactone A was built and geometrically optimized using PRODRG program.

In still another embodiment of the present invention, wherein i) a process is developed for producing meroterpenoid compounds in an efficient, fast and economic way, and ii) *Aspergillus terreus* strain MTCC 5390 is chosen as the preferred species in the present study on account of its inertness, which renders it easy and safe to handle in the laboratory and in commercial scale fermentations.

A process according to the invention comprises the submerged cultivation of ascomycetes fungi, producers of meroterpenoid, belonging to the genus *Aspergillus* on a nutrient media including nitrogen, mineral salts and a source of carbon as mono-, or di-saccharides including glucose or sucrose; one-step isolation procedure from a fermentation broth obtained from the submerged culture under static conditions.

A process for isolation of terreulactone A from the fungus *Aspergillus terreus* strain MTCC 5390 and the said process comprising of the steps of:
 a) Extracting the fungal biomass with an organic solvent
 b) Filtering the extract of step (a) through a Whatman filter paper to obtain clear solution
 c) Evaporating the solution of step (b) under vaccum to obtain crude extract.
 d) Purifying the crude extract of step (c) by reversed phase high performance chromatography (RP-HPLC).

The purified compound was analyzed through electrospray ionization mass spectrum (ESI-MS) having molecular weight 511.1 (M+H)$^+$.

In still another embodiment of the present invention, the insecticidal activity of the compound tested against *Helicoverpa arinigera*, significantly reported as national pest for most of the agricultural crops.

The present invention focuses the use of meroterpenoids as an insecticide. There are no report for application of meroterpenoids especially terreulactones for crop protection. Hence, the inventors made an approach to develop these bioactive compounds as potent insecticides. Terreulactone A has been known for its application in the treatment of Alzhemier's disease, as a neuroactive drug. However, the property of bioactive molecule has not been exploited for the development of insecticidal agents or biorationals (soft pesticides) to control wide range of Insect pests. Terreulactone A has a high level of efficacy for lepidopteran larvae, as well as some Diptera, Coleoptera, Thysanoptera, and Hymenoptera, but has limited to no activity to other insects and exhibits low toxicity to mammals and other wildlife.

In the present invention, the plant or plant parts were treated with terreulactones and larval pests were allowed to feed the plant or plant parts (which may be leaves, roots, stem, flowers etc). It was observed that the terreulactone A increased the mortality rate of the larval pests indicating its potent insecticidal activity. The mode of application of terreulactone on the plant system is through either contact or systemic action. The mode of action on the insects is by partial paralysis.

The present invention also aims towards the development of terreulactone through liquid fermentations. Hence the approach of the present disclosure has several advantages over solid state fermentation, in terms of process control during industrial scale up and commercialization.

The strain *Aspergillus terreus* is cultured in an aqueous media such as those employed for good mycelium growth and biomass accumulation for production of terreulactones. Such media contain sources of carbon, nitrogen and inorganic salts assimilated by the growing culture. All strains *Aspergillus terreus* are capable of utilizing monosaccharide and disaccharides that are good sources of carbon for their growth. Glucose and sucrose are the main ingredients that were used either alone or in combination as sources of carbon. The amount of carbohydrate usually varies between about 1.5% and 6% by weight of the medium to provide a high yield of biomass. The fermentation is carried out at temperatures ranging from 28 deg C. to 35 deg C. for a period of 7 days. The optimal temperature for growth is 30 deg C.; further increase of temperature beyond 35 deg C. is detrimental for fungal biomass formation.

The invention is further elaborated with the help of following examples and figures. However, these examples and figures should not be construed to limit the scope of invention.

EXAMPLE 1

Homology Modeling of Acetylcholinesterase from *Helicoverpa Armigera*

Figure 1:
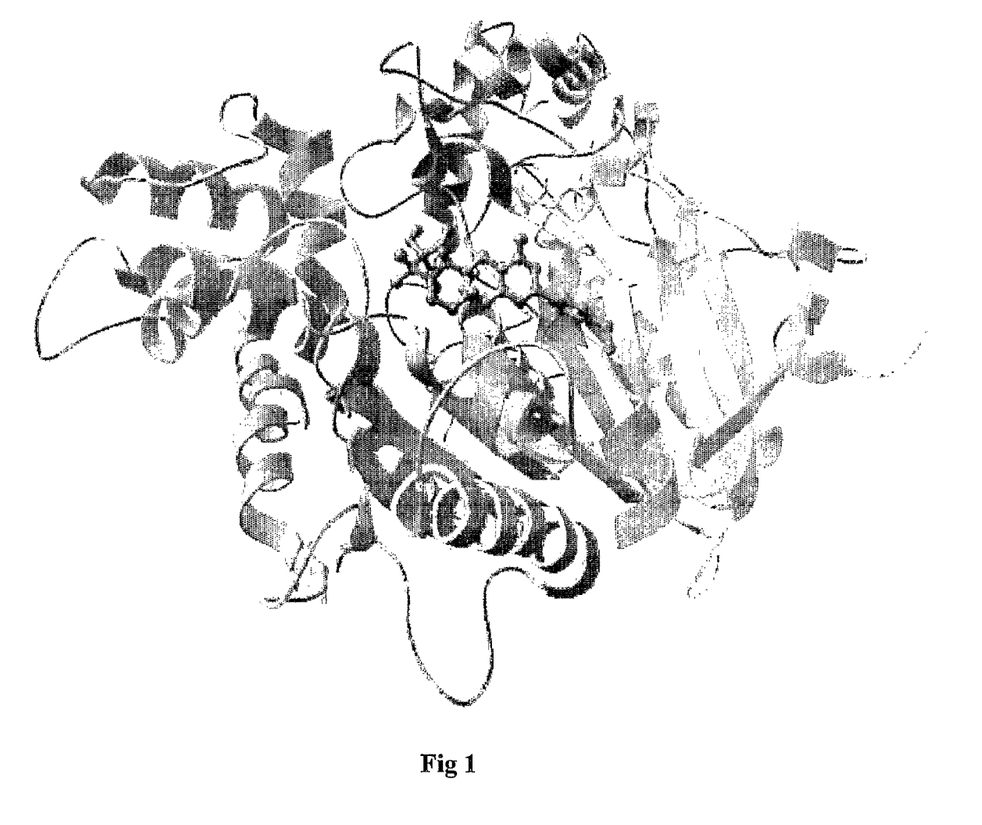
FIG. 1: The conformation of *Drosophila* acetyl choline esterase (Ach) receptor-terreulactone complex developed through molecular docking approach. The estimated binding free energy of Ach-receptor and terreulactone A complex is −8.35 kcal/mol and empirical inhibition constant (Ki) is 764 nano mole.

The construction of homology model for acetylcholinesterase from *H. armigera* was done by MODELLER program. The structural template used for this study was experimental structure of *Drosophila melanogaster* acetylcholinesterase (FIG. 1). The acetylcholinesterase amino acid sequence matches with structural template from 60-640 regions. The matched portion of *Helicoverpa* acetylcholinesterase 3D structure was built. The good model was evaluated by PROCHECK suite. The quality of 3D model was assessed in terms of Ramachandran stereo chemical plot. The 90% of amino acid residues falling on most favorable region is considered as good quality model.

EXAMPLE 2

Molecular Docking Studies

*Helicoverpa* is one of the important pest need to be studied. In silico based docking was performed on acetylcholinesterase for evaluating binding affinities. Better way of understanding molecular interaction would provide valuable information about de novo synthesis of meroterpenoid analogs. The molecular docking compounds such as Terreulactone were built and geometrically optimized using PRODRG program. In AutoDock3.0.5 suite, the search method used was Lamarckian genetic algorithm (LGA) with 50 LGA runs. The number of individuals in each population was set at 300. The maximum number of energy evaluations was set at 10000000 and the maximum number of generations was set at 50,000.

Figure 2:
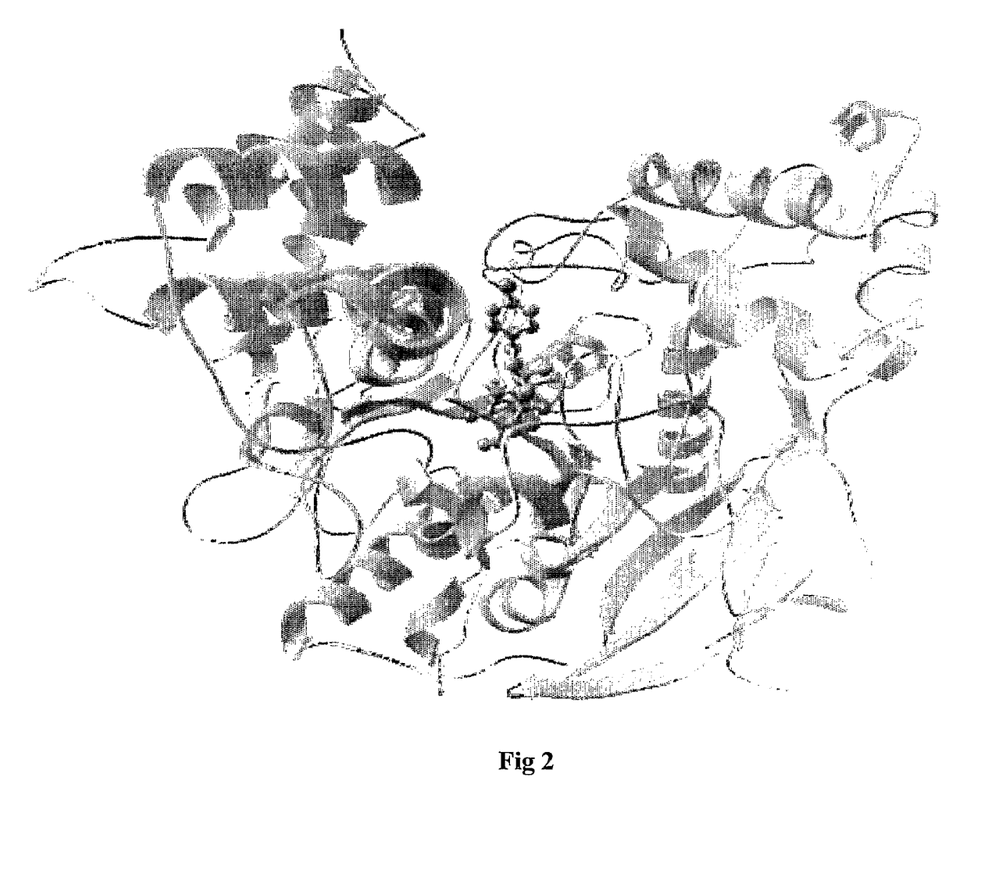
FIG. 2: The conformation of *Helicoverpa armigera* acetyl choline esterase (Ach) receptor-terreulactone complex developed through molecular docking approach. The estimated binding free energy of Ach-receptor and terreulactone A complex is −11.38 kcal/mol and empirical inhibition constant (Ki) is 4.58 nano mole.

FIG. 2 shows the conformation of *Helicoverpa armigera* acetyl choline esterase (Ach) receptor-terreulactone complex developed through molecular docking approach. The estimated binding free energy of Ach-receptor and terreulactone A complex is −11.38 kcal/mol and empirical inhibition constant (Ki) is 4.58 nano mole.

EXAMPLE 3

Source and Culturing of *Aspergillus terreus* Strains on Liquid Medium

Soil samples from various regions of Karnataka (India) were used to isolate the fungal strains as per the method of Seifert, 1990. The *Aspergillus terreus* isolates were maintained on potato dextrose slants and identified as per Raper and Fennell (1965).

| Potato Dextrose Agar (PDA) | |
|---|---|
| Potato* | 200.0 g |
| Dextrose | 20.0 g |
| Agar | 15.0 g |
| Distilled water | 1 liter |

Boiled diced potatoes in 500 ml of water until thoroughly cooked, filter through cheese cloth. Add dextrose to the filtrate and adjust the pH to 4.5 units. Dissolve agar in water and bring up the required volume by the addition of water. Autoclave the contents at 15 lb pressure for 15 minutes.

The strain *Aspergillus terreus* can also be cultured using:

| Czapek - Dox Agar | |
|---|---|
| K2HPO4 | 1.0 g |
| NaNO3 | 3.0 g |
| KCl | 0.5 g |
| MgSO4•7H2O | 0.5 g |
| FeSO4•7H2O | 0.01 g |
| Sucrose | 30.0 g |
| Agar | 15.0 g |
| Distilled water | 1 liter |

All the ingredients are dissolved except phosphate in half of the water and sucrose was added. pH was adjusted to 6.3 units and the volume is made upto 1 litre.

| Sabouraud's Agar | |
|---|---|
| Peptone | 10.0 g |
| Dextrose | 40.0 g |
| Agar | 15.0 g |
| Distilled water | 1 liter |
| Adjust pH to | 5.6 |

Meroterpenoid screening medium having the following composition was used—Sucrose 15 g/L, Vogel's minimal medium 20 ml/L, distilled water 1000 mL. The pH of the medium was adjusted to 4.5 units. The sterile medium was transferred into 10 mL culture tubes and inoculated with 10 days old fungal spores. The inoculated test tubes were incubated at 30 deg C. for 7 days.

| Vogel's terreulactone production medium | |
|---|---|
| Vogel's salts (50X) | 20 ml |
| Sucrose | 15 g |
| Distilled water | 1 liter |
| pH | 4.5 Units |

| Vogel's Salts (50X) | |
|---|---|
| Na3 Citrate | 150.0 g |
| $KH_2PO_4$ | 250.0 g |
| $NH_4NO_3$ | 100.0 g |
| $MgSO_4•7H_2O$ | 10.0 g |
| $CaCl_2•2H_2O$ | 5.0 g |
| Trace element solution[1] | 5.0 ml |
| Biotin solution[2] | 2.5 ml |
| Distilled water | 1 liter |

| Trace element solution[1] | |
| --- | --- |
| Citric acid | 5.0 g |
| $ZnSO_4 \cdot 7H_2O$ | 5.0 g |
| $Fe(NH4)_2(SO4)_2 \cdot 6H_2O$ | 1.0 g |
| $CaSO_4 \cdot 5H_2O$ | 0.25 g |
| $MnSO_4 \cdot 1H_2O$ | 0.05 g |
| $H3BO_3$, anhydrous | 0.05 g |
| $Na_2MoO_4 \cdot 2H_2O$ | 0.05 g |
| Distilled water | 100 ml |
| Biotin solution[2] | |
| Biotin | 5.0 mg |
| Distilled water | 50 ml |

EXAMPLE 4

Liquid Fermentation Process for Meroterpenoid Production

A culture tube with a 8-10 days old pure culture of *Aspergillus terreus* strain MTCC 5390 was used for inoculation into 100 ml of medium A in a 250 ml Erlenmeyer flask. Medium A has the following composition (g/L): Composition of Vogel's minimal medium and pH of the medium was adjusted to 4.5 units. The contents of medium were sterilized to 120 deg C. for 20 minutes. The inoculated flasks were incubated at stationary conditions of growth in a temperature chamber at 30 deg C. After 7 days of growth, a mycelium mat covered all the surface of the culture medium.

EXAMPLE 5

Extraction of Meroterpenoids and Assay

The fungal mycelium obtained after 6 days of incubation was filtered and dried in between folds of sterilized bottling paper. The dried biomass obtained was extracted with ethylacetate in the ratio of 1:10 and kept at constant shaking for 30 min. The extracted biomass was filtered to remove debris and concentrated in vacuum drier at the temperature range of 30 deg C. to 45 deg C. The oily, viscous compound obtained was used for meroterpenoid assay.

EXAMPLE 6

Analysis of Meroterpenoids Using High Performance Liquid Chromatography (HPLC)

Attempts were also made to confirm the meroterpenoids from fermented mycelium through HPLC method. The biomass obtained after fermentation process was washed with water and extracted with ethylacetate and filtered through 0.45 µm filter. Ten mL of organic phase was dried under vacuum at 45 deg C. The dried residues were dissolved with methanol and water (8:2, v/v). HPLC was carried out using $C_{18}$ reverse phase column thermostated at 30 deg C. The column was developed at a flow rate of 0.5 mL/min for 30 min with acetonitrile and water (50:50, v/v). The chromatograms were monitored at 300 nm and later identified by their retention time and ESI-mass spectrum.

Figure 4:
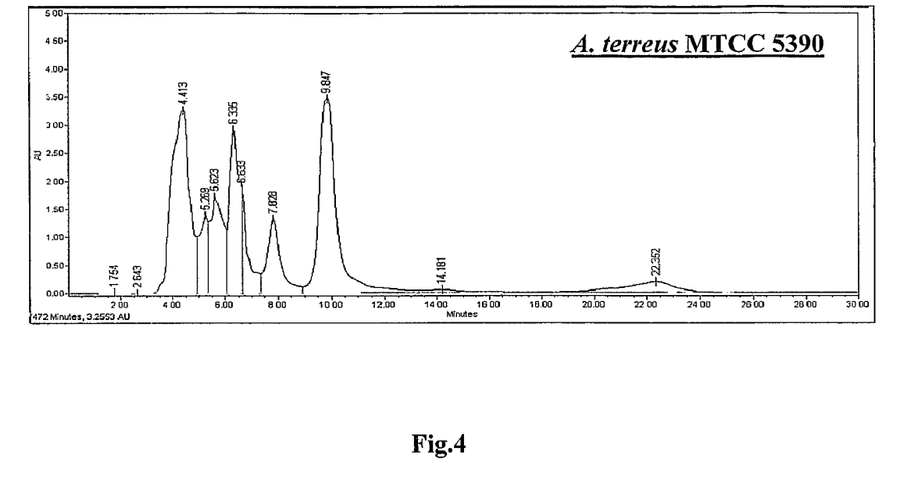
FIG. 4: The HPLC profile of *Aspergillus terreus* culture MTCC 5390 grown under liquid fermentation and terreulactone A separated at retention time of 9.8 minutes.

FIG. 4 shows the HPLC profile of *Aspergillus terreus* culture MTCC 5390 grown under liquid fermentation and terreulactone A separated at retention time of 9.8 minutes.

EXAMPLE 7

Determination of Meroterpenoids Through Matrix-Assisted Laser Desorption Ionization (MALDI)—Electrospray Ionization (ESI) Mass Spectrometric Analysis HPLC purified meroterpenoid samples were subjected to MALDI-ESI analysis. MALDI mass spectrometric analysis was performed on a Kratos PC Kompact Seq 1.2.2 mass spectrometer in the linear mode.

Figure 3:
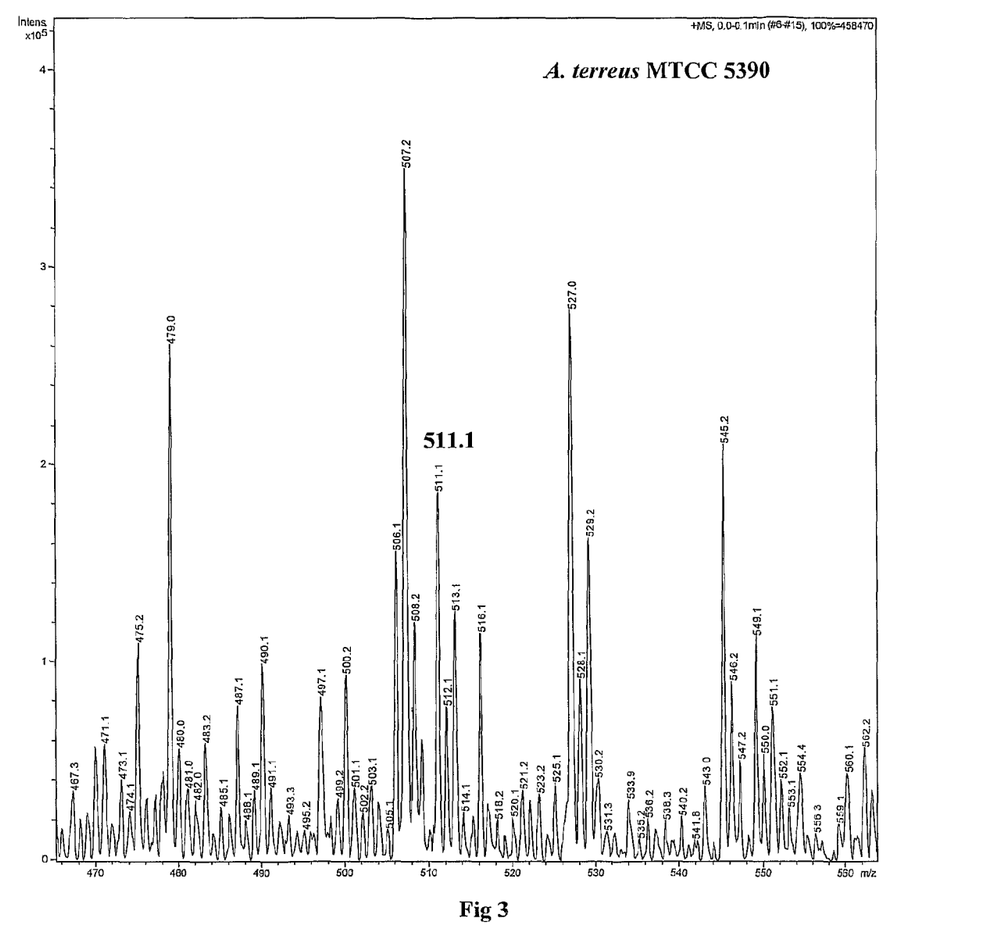
FIG. 3: Electrospray ionization mass spectrum of terreulactone A [511.1 (M+H)$^+$] obtained from ethylacetate extract of *Aspergillus terreus* MTCC 5390.
Figure 5:
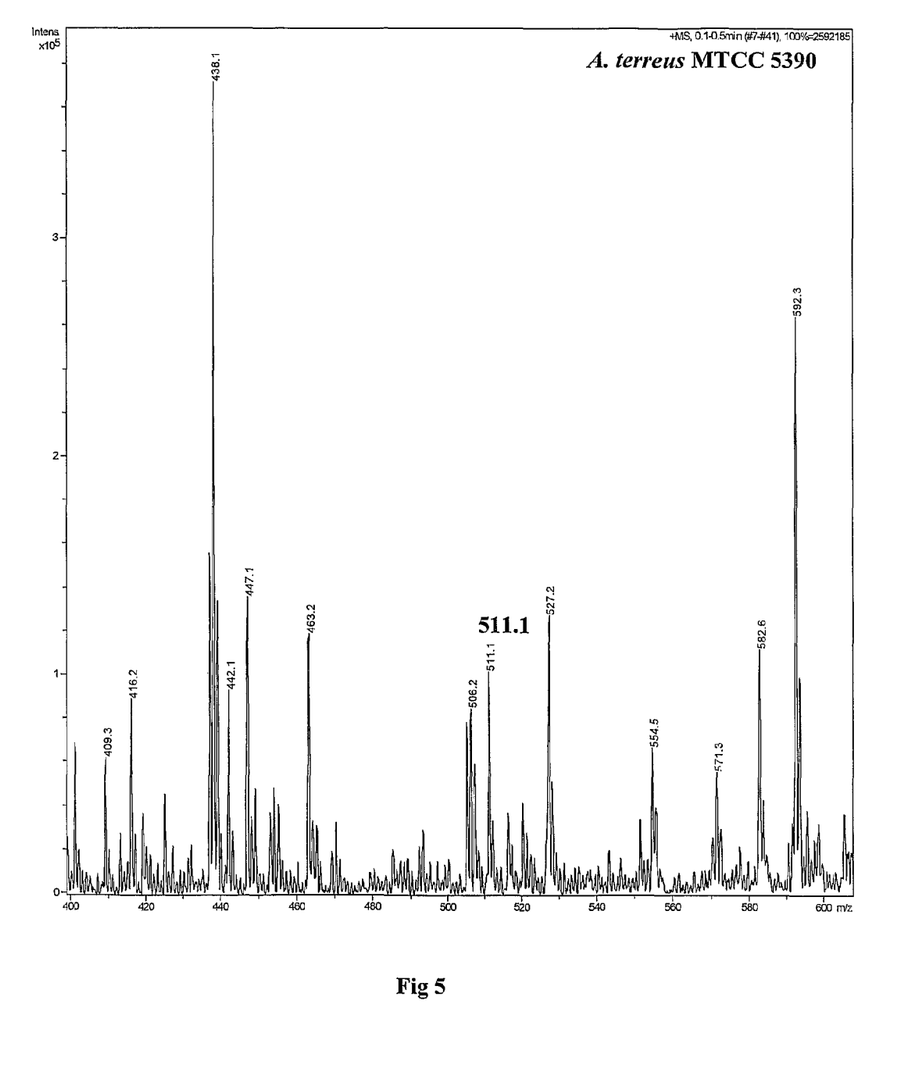
FIG. 5: Electrospray ionization mass spectrum of terreulactone A [511.1 (M+H)$^+$] obtained from HPLC purified ethylacetate extract of *Aspergillus terreus* MTCC 5390.

FIGS. 3 & 5 shows electrospray ionization mass spectrum of terreulactone A [511.1 $(M+H)^+$] obtained from HPLC purified ethylacetate extract of *Aspergillus terreus* MTCC 5390.

EXAMPLE 8

Bioassay of Meroterpenoid Using *H. armigera* Larvae

The cotton Bollworm, *Helicoverpa armigera* is considered as one of the major threats to present day intensive agriculture. Hence, experiments were designed to know the efficacy of meroterpenoid (terreulactone A) obtained from *Aspergillus terreus*. Cotton leaves were surface sterilized with 0.5% sodium hypochlorite, rinsed in sterile water and shade dried. The leaves were dipped in respective concentration of the insecticide for 30 seconds and then they were drained and dried at room temperature. The turgidity was maintained by surrounding the petiole with cotton wool saturated with water. The petioles of the leaves with cotton swab were kept immersed in water and were used control. The entire setup was kept enclosed in mylar film cage and *Helicoverpa armigera* larvae (third instar) of 30-40 milligrams weight were allowed to feed. Mortality rate was recorded at 24 hours intervals up to 6 days. The evaluation of terreulactone A on *Helicoverpa armigera* insect larvae is given in Table 1.

TABLE 1

Evaluation of terreulactone A on *Helicoverpa armigera* insect larvae

| | *H. armigera* larvae | |
| --- | --- | --- |
| Terreulactone A (µg) | Mortality (%) | Survival (%) |
| 0 | 0 | 100 |
| 2.5 | 52.5 | 47.5 |
| 5.0 | 62.5 | 37.5 |
| 10 | 82.5 | 17.5 |

REFERENCES

1) Cho K M, Kim W G, Lee C K and Yoo I D (2003). Terreulactones A, B, C and D: Novel acetyl choline esterase inhibitors produced by *Aspergillus terreus*.

2) Raper K B and Fennell D I (1965) The genus *Aspergillus*, Williams and Wilkins, New York; 567-577.

3) Rajasekharan R, Rodrigues R and Reddy S. U.S. Pat. No. 6,277,786.

4) Seifert K A (1990) Isolation of filamentous fungi, In: Isolation of biotechnological organisms from nature (David P L ed), McGraw-Hill, New York; 21-51.

We claim:

1. A method of protecting plant(s) against larval pests, said method comprising treating the plant(s) with a composition consisting essentially of an effective amount of a terreulactone selected from the group consisting of terreulactone A, terreulactone B, terreulactone C, terreulactone D, and combinations thereof.

2. The method as claimed in claim 1, wherein the larval pests are selected from a group consisting of lepidoptera, diptera, coleoptera, thysanoptera and hymenoptera.

3. The method as claimed in claim 1, wherein the larval pest is *Helicoverpa armigera*.

4. The method as claimed in claim 1, wherein the terreulactone provides for about 80% to about 85% mortality rate at a concentration of about 8 µg to about 12 µg.

5. The method as claimed in claim 1, wherein the terreulactone is terreulactone A.

6. The method as claimed in claim 2, wherein the larval pests are lepidoptera.

7. The method as claimed in claim 4, wherein the terreulactone provides for about 80% to about 85% mortality rate at a concentration of 10 µg.

* * * * *